United States Patent [19]

Fritch

[11] Patent Number: 4,906,247

[45] Date of Patent: Mar. 6, 1990

[54] INTRAOCULAR LENS INSERTION SYSTEM

[76] Inventor: Charles D. Fritch, Rte. 11, P.O. Box 239B, Bakersfield, Calif. 93308

[21] Appl. No.: 318,833

[22] Filed: Mar. 6, 1989

[51] Int. Cl.[4] .......................... A61F 2/16; A61B 17/00
[52] U.S. Cl. ........................................ 623/6; 606/107
[58] Field of Search ............................. 623/6; 606/107

[56] References Cited

U.S. PATENT DOCUMENTS

| | | | |
|---|---|---|---|
| 4,681,102 | 7/1987 | Bartell | 623/6 X |
| 4,747,404 | 3/1988 | Jampel et al. | 606/107 |
| 4,769,034 | 9/1988 | Poley | 623/6 |
| 4,785,810 | 11/1988 | Baccala et al. | 606/107 |
| 4,813,957 | 3/1989 | McDonald | 623/6 |
| 4,836,201 | 6/1989 | Patton et al. | 606/107 |

Primary Examiner—Ronald L. Frinks
Attorney, Agent, or Firm—Singer & Singer

[57] ABSTRACT

A system and method for folding a soft, plastic intraocular lens (IOL) for use by surgeons as a replacement for a person's cataractic lens. The lens is placed on a jig. The surgeon inserts a pair of forceps into a hollow soft plastic tube which is stretched by opening the forceps. The stretch plastic tube is placed over the lens while the surgeon releases the forceps and folds the tube about the lens thereby folding the lens within the stretched hollow tube. The folded lens and tube is inserted through a suitable incision within the eye and the lens allowed to unfold. The hollow tube is removed and the lens positioned as determined by the surgeon.

28 Claims, 2 Drawing Sheets

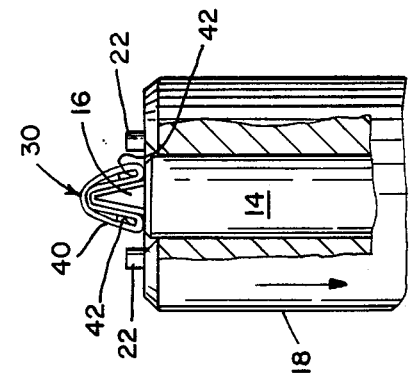
Fig. 10.
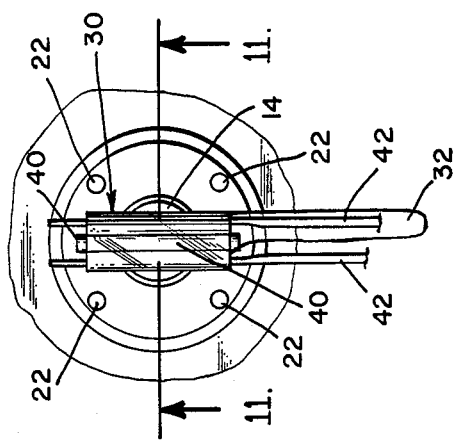
Fig. 11.
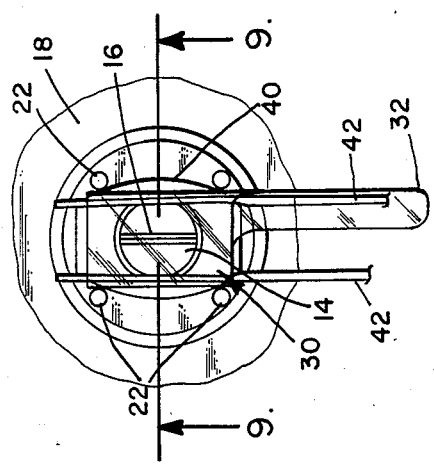
Fig. 8.
Fig. 9.
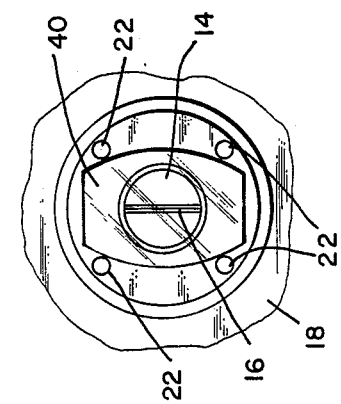
Fig. 6.
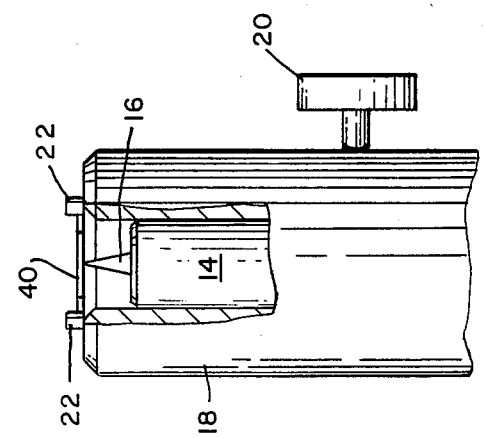
Fig. 7.

INTRAOCULAR LENS INSERTION SYSTEM

This invention relates to a method and apparatus for folding an intraocular lens, also called an IOL lens, and more particularly to a system for folding and inserting a folded IOL within the eye that requires a smaller incision for insertion and one that is easy for the surgeon to handle.

In the art as practiced today, the IOL lens has found great popularity among ophthalmologists and patients alike for the treatment of cataracts which have the effect of clouding over and becoming opaque thereby preventing the patient from seeing.

A cataract condition is sometimes defined as a general loss of transparency in which the lens which is located within the capsule becomes opaque thereby preventing light from passing through to the optic nerve. The more opaque the lens the less vision for the patient.

The present invention is primarily concerned with minimizing the incision necessary to insert the IOL. Folding the IOL has the obvious advantage of reducing the size of the incision necessary to insert the IOL provided the lens can be folded properly and inserted without further trauma to the patient.

The development of intraocular lens plantation for the correction of aphakia following cataract surgery has lead to a high degree of technology development in Ophthalmology. The implantation of plastic lenses within the eye through a relatively large incision following intracapsular susrgery has gradually undergone change from approximately a 11 mm. corneoscleral incision to approximately a 6 to 7 mm. incision for the entry side of the intraocular lens.

The actual removal of the cataract prior to the implantation of the intraocular lens or the pseudophakic implant now requires a much smaller incision through the development of new technology for the removal of the cataract. The actual removal of the cataract prior to the implantation has gone from approximately 11 mm. incision for intracapsular cataract surgery to approximately a 3 mm. or 3.2 to a 3.4 mm. incision with the use of ultrasonic hand pieces or phacoemulsification techniques.

This small 3 mm. incision or 3.4 mm. incision has been gradually enlarged beneath the scleral pocket incision to allow the insertion of the larger intraocular lenses which have been developed and which have measured anywhere from 5, 5.5, 6, 6.5 and up to approximately 7.0 mm. in diameter. Because of the advent of what is now termed "small incision cataract surgery" due to phacoemulsification, more and more surgeons and manufacturers have looked for an intraocular lens which may be inserted through a small cataract incision.

There has been extensive progress and investigation both in silicone and hydrogel material as well as other soft material to allow other development and research in small incision implantation research to allow the insertion of an intraocular lens through a relatively small 3 to 3.4 to 3.6 mm. incision.

A 4 mm. incision should be able to accomodate a lens with approximately a 6 to 7 mm. or larger diameter. One of the main problems with the small incision implantation techniques have been the difficulty with developing a lens which can either be folded or molded or made smaller in diameter for insertion through these small incisions.

Various attempts have been made by investigators to provide techniques for folding and inserting a folded lens in the eye. These techniques have included "shooters" which insert the folded lens under pressure. There are many drawbacks in this area, the most important being a lack of control over the injection of the lens into the eye. In addition, an excessive or large amount of visco elastic material for protecting the cornea in the internal structure of the eye is required while the lens is being inserted. This sudden injection of these lenses into the eye have resulted in a nonacceptable high incidence of complications such as corneal injuries or dislocation of the lenses being shot through the back lens capsule or into the interior of the eye itself into the vitreous cavity and being misplaced at the time of insertion.

Following the initial attempts with shooters and injector type instruments, surgeons have once again returned to control manual forcep entry. The difficulty with the many forceps that have been developed such as the Faulkner Forceps as well as other forceps is that the forceps themselves require a rather large amount of space to enter into the eye and they require some stretching of tissue both in the anterior/posterior direction as well as lateral direction.

These instruments also have been somewhat damaging to the soft material themselves to either the silicone or the hydrogel materials that are presently being utilized and it appears that they may be difficult to utilize for future materials in this area.

The present invention is an improvement over these previous techniques in that a folding technique has been developed with the use of a folding block as well as small delicate angle forceps and the utilizing also of a "bag" made of a soft material either silicone or polyethylene or hydrogel material. A variety of substances can be used to create this small, very thin-like hollow bag which is placed over the forceps. With the use of this bag and the very delicate angle folding forceps, the soft lens material can be gently folded over the block or placed on the block, and with the folding bar pushed upward as the outer sleeve is pushed down this allows the safe and effective folding of the lens.

The folding block and bar as well as the silicone bag or polyethylene bag, as well as a variety of forceps can be utilized. These long, delicate forceps allows the lens to be gently folded under the protection of the bag without direct damage to the soft intraocular lens material. Also, these delicate forceps increase the ease of entry and safety of the entry of the lens. It requires less visco elastic material and has allowed a smaller incision of 3.4 to 3.6 mm. which allows limited or small incision wound entry and single stitch closure of the wound.

Both the anterior/posterior direction of these forceps as well as the ease of the insertion and control of the lens both opening in a downward direction of the soft pseudophakic implant can be opened in a downward direction posteriorly and under complete control. The small, thin wall sack which is used for protection of the lens, aids in folding of the lens. The sack can easily be removed by a small tail or tab of material that is externally located following its insertion into the anterior and directly into the posterior chamber. Whether the lenses are round which, is demonstrated with the AMO type lens with PROLENE (polypropylene) loops or whether the lens folder is utilized for the hydrogel lens which does not presently have loops, appears to make essentially no difference in the ease of folding and inserting the lens.

Further objects and advantages of the present invention will be made more apparent by referring now to the drawings wherein:

FIG. 6 is a top view of the jig illustrated in FIG. 1;

FIG. 7 is a partial sectional view of FIG. 6;

FIG. 8 is a top view of the jig illustrated in FIG. 1 showing the first step in folding the lens;

FIG. 9 is a sectional view taken along lines 9—9 of FIG. 8;

FIG. 10 is a top view of the jig illustrated in FIG. 1 showing the second step of folding the lens; and FIG. 11 is a sectional view of FIG. 10 taken along lines 11—11.

In the present invention, there is described a method and apparatus that allows the surgeon to fold the lens without damaging the lens and at the same time allows the folded lens to be safely inserted without injury or trauma to the patient.

Figure 1:
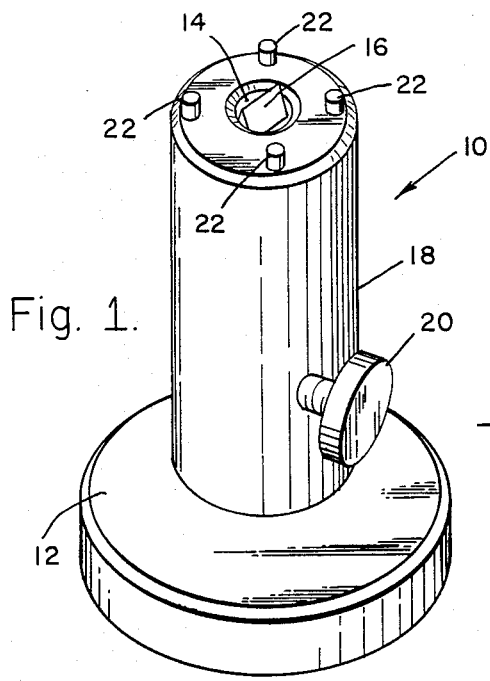
FIG. 1 is a perspective view of a jig used to fold the IOL.
Figure 2:
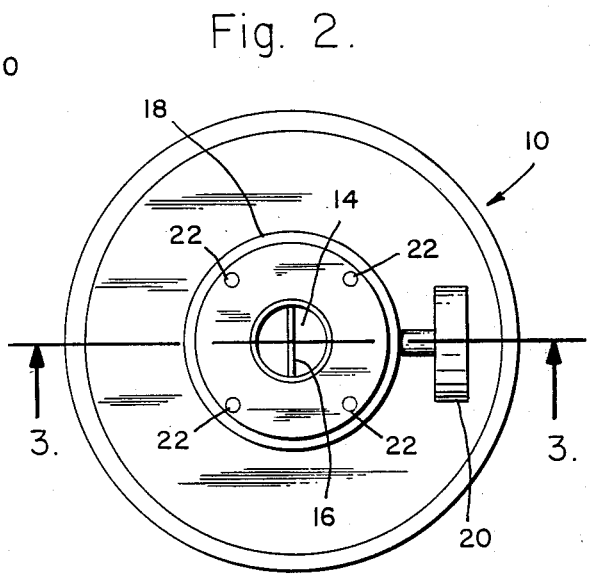
FIG. 2 is a top view of the jig illustrated in FIG. 1.
Figure 3:
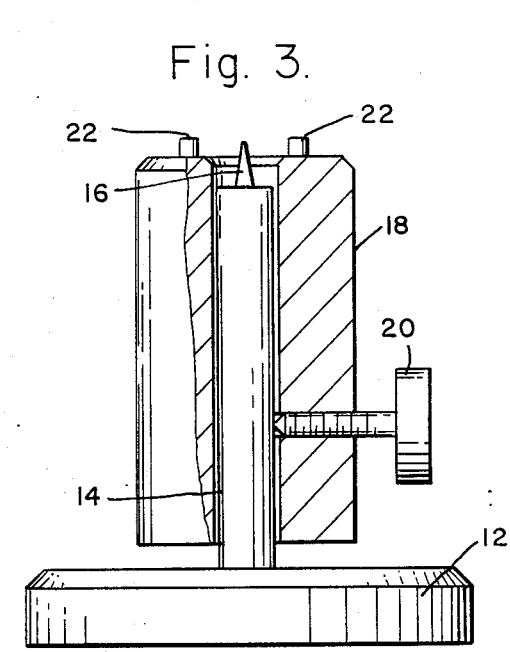
FIG. 3 is a section 3—3 of FIG. 2.

Referring now to FIGS. 1, 2 and 3, there is shown a folding block 10 comprising a stationary platform 12 fixedly attached to a plunger 14 having a knife edge 16 attached to the upper edge of the plunger 14. A movable cylinder 18 having a suitable locating device such as a set screw 20 is adapted to move in an up and down direction about the fixed plunger 14. The set screw 20 allows the operator to locate the cylinder 18 in any preferred position relative to the plunger 14. Located on the uppermost portion of the cylinder 18 are a plurality of locating pins 22 adapted to locate and hold an IOL in a substantially flat position on the top of the cylinder 18.

In the preferred use of the folding block 10, the operator will loosen the set screw 20 and raise the cylinder 18 to a height that allows the top of the cylinder 18 to clear the top of the knife edge 16. In this position, an IOL is placed on the top of the cylinder 18 and between the locating pins 22. The actual operation of the folding block 10 will be described in connection with FIGS. 6 through 11.

Figure 4:
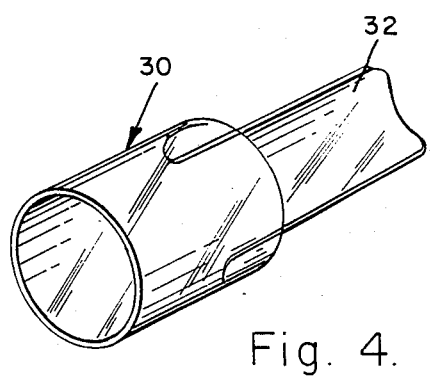
FIG. 4 is a perspective view of the hollow tube used to protect the IOL.
Figure 5:
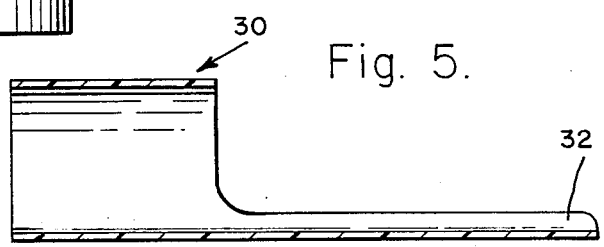
FIG. 5 is a cross sectional view of FIG. 4.

Referring now to FIGS. 4 and 5, there is illustrated a hollow plastic tube 30 having a diameter substantially equal to the diameter of the IOL being used. The tube 30 is a flexible plastic tube having a tab 32 located at one end which is used by the surgeon as a handle as will be described later. In practice the tube 30 will be placed around the IOL so a to protect the IOL from the doctor's forceps when the IOL is folded and inserted into the eye of the patient.

The first step in the method is to properly fold the IOL and in a manner that does not injure or damage the lens itself.

Referring now to FIGS. 6 and 7, there is shown how the adjusting screw 20 is first loosened in order to move the cylinder 18 in an upward position so that the top of the cylinder 18 is extended above the top of the knife edge 16.

A suitable, soft plastic IOL 40 is placed on top of the movable cylinder 18 so as to be located within the locating pins 22. In this position, the IOL 40 is located on top of the cylinder 18, clear of the knife edge 16.

In order for the physician to properly protect the IOL 40, the surgeon first inserts the ends of his forceps 42 as shown in FIG. 8, through the opening of the hollow tube 30, and from the side having the tab 32.

The surgeon then separates the forceps thereby stretching the tube 30 a distance that is slightly greater than the largest diameter of the IOL 40. Present day IOL's have a diameter of approximately 6 mm. in width and a length of approximately 12 mm. The plastic tube 30 is stretched to approximately 8 mm. and the stretched hollow tube 30 placed over the IOL 40 as shown in FIG. 8.

As shown in FIGS. 9, 10 and 11, the surgeon presses the expanded tube 30 against the IOL 40 and at the same time loosens the set screw 20 as shown in FIG. 9. This allows the cylinder 18 to move in a downward direction, and as the doctor pushes the expanded tube 30 against the IOL, also in a downward direction, the cylinder 18 moves, thereby forcing the knife edge 16 on the plunger 14 to push upwards against the IOL 40 thereby causing the IOL and the expanded tube 30 to fold about the knife edge 16. In this position the surgeon closes the forceps against the knife edge 16 thereby folding the IOL 40 within the stretched tube 30.

The surgeon now takes the folded lens 40 and folded tube 30 and inserts the folded IOL together with the folded tube into the eye through the same incision that was made to remove the cataract. By releasing his pressure on the forceps, the IOL 40 and the tube 30 are allowed to open to their full size. The doctor easily removes the tube by means of a tab 32 and then repositions the IOL 40 in the eye within the capsule.

The incision made by the surgeon in the eye to remove the cataract does not have to be enlarged to accept the IOL thereby reducing the trauma to the eye and reducing the greater effect of infection that would be necessary if a larger incision had to be made to insert the present day IOL's.

I claim:

1. A method for protecting and folding an IOL for insertion into an eye comprising the steps of:
   placing a soft IOL on a flat surface;
   then inserting the operating ends of a pair of forceps into a hollow plastic tube and separating the forceps thereby stretching the tube;
   then placing the stretched tube over the IOL; and
   then closing the forceps about the IOL thereby folding the IOL within the stretched tube.

2. A method according to claim 1 in which said plastic tube has a tab located on only one side and in which said forceps are inserted into the hollow tube from the side having the tab.

3. A method according to claim 1 in which the hollow plastic tube is stretched an amount greater then the diameter of the IOL.

4. A method for protecting and folding an IOL for insertion into an eye comprising the steps of:
   placing a soft IOL on a movable cylinder encompassing a fixed centrally located plunger having a knife edge;
   locating the IOL on the movable cylinder over the knife edge;
   then inserting the operating ends of a pair of forceps into a hollow plastic tube and separating the forceps thereby stretching the tube;
   then placing the stretched tube over the IOL and pushing the stretched tube in a downward direction against the IOL thereby causing the cylinder to move in a downward direction causing the IOL to fold about the knife edge located on the fixed plunger; and then closing the forceps about the knife edge thereby folding the plastic tube about the folded IOL.

5. A method according to claim 4 in which said plastic tube has a tab located on only one side and in which said forceps are inserted into the hollow tube from the side having the tab.

6. A method according to claim 4 in which the hollow plastic tube is stretched an amount greater then the diameter of the IOL.

7. A system for protecting and folding an IOL for insertion into an eye comprising:
means for placing a soft IOL on a flat surface;
means for inserting the operating ends of a pair of forceps into a hollow plastic tube and separating the forceps thereby stretching the tube;
means for placing the stretched tube over the IOL; and
means for closing the forceps thereby folding the lens within the stretched tube.

8. A system according to claim 7 in which said hollow plastic tube has an extended tab located on only one side.

9. A system according to claim 8 in which said forceps are inserted into the hollow tube from the side having the tab.

10. A system for protecting and folding an IOL for insertion into an eye comprising:
means for placing a soft IOL on a movable cylinder encompassing a fixed centrally located plunger having a knife edge;
means for locating the IOL on the movable cylinder over the knife edge;
means for inserting the operating ends of a pair of forceps into a hollow plastic tube and separating the forceps thereby stretching the tube;
means for placing the stretched tube over the IOL and pushing the stretched tube in a downward direction against the IOL thereby causing the cylinder to move in a downward direction causing the IOL to fold about the knife edge located on the fixed plunger; and
means for closing the forceps about the knife edge thereby folding the plastic tube about the folded IOL.

11. A system according to claim 10 in which said IOL is supported over said plunger on a plurality of raised support members fixedly attached to said movable cylinder.

12. A system according to claim 10 which includes friction means for movably supporting said movable cylinder against said fixed plunger for allowing said movable cylinder to maintain a selected position relative said plunger.

13. A system according to claim 10 in which said hollow plastic tube has an extended tab located on only one side.

14. A system according to claim 13 in which said forceps are inserted into the hollow tube from the side having the tab.

15. A method for folding and inserting a folded IOL into an eye comprising the steps of:
placing a soft IOL on a flat surface;
then inserting the operating ends of a pair of forceps into a hollow plastic tube and separating the forceps thereby stretching the tube;
then placing the stretched tube over the IOL;
then closing the forceps about the IOL thereby folding the IOL within the stretched tube;
then inserting the forceps containing the folded lens and the tube into the eye through a suitable incision;
then opening the forceps thereby allowing the lens and the hollow tube to unfold; and
then using the forceps to remove the plastic tube and reposition the lens.

16. A method according to claim 15 in which said plastic tube has a tab located on only one side and in which said forceps are inserted into the hollow tube from the side having the tab.

17. A method according to claim 16 in which the plastic tube is removed from the eye by pulling on the tab with the forceps.

18. A method according to claim 15 in which the hollow plastic tube is stretched an amount greater then the diameter of the IOL.

19. A method for folding and inserting an IOL into an eye comprising the steps of:
placing a soft IOL on a movable cylinder encompassing a fixed centrally located plunger having a knife edge;
locating the IOL on the movable cylinder over the knife edge;
then inserting the operating ends of a pair of forceps into a hollow plastic tube and separating the forceps thereby stretching the tube;
then placing the stretched tube over the IOL and pushing the stretched tube in a downward direction against the IOL thereby causing the cylinder to move in a downward direction causing the IOL to fold about the knife edge located on the fixed 14 plunger;
then closing the forceps about the knife edge thereby folding the plastic tube about the folded OL;
then inserting the folded lens and the tube through a suitable incision in the eye;
then opening the forceps allowing the lens and the hollow tube to unfold; and
then removing the hollow tube and repositioning the lens.

20. A method according to claim 19 in which said plastic tube has a tab located on only one side and in which said forceps are inserted into the hollow tube from the side having the tab.

21. A method according to claim 20 in which the plastic tube is removed from the eye by pulling on the tab with the forceps.

22. A method according to claim 20 in which the hollow plastic tube is stretched an amount greater then the diameter of the IOL.

23. A system for folding and inserting a folded IOL into an eye comprising:
means for placing a soft IOL on a flat surface;
means for inserting the operating ends of a pair of forceps into a hollow plastic tube and separating the forceps thereby stretching the tube;
means for placing the stretched tube over the IOL;
means for closing the forceps about the IOL thereby folding the IOL within the stretched tube;
means for inserting the forceps containing the folded lens and the tube into the eye through a suitable incision;
means for opening the forceps thereby allowing the lens to unfold; and means for removing the plastic tube and reposition the lens.

24. A system according to claim 23 in which said plastic tube has a tab located on only one side and in which the forceps are inserted into the hollow tube from the side having the tab.

25. A system according to claim 24 in which said hollow tube is removed by pulling on the tab.

26. A system for folding and inserting an IOL into an eye comprising :
   means for placing a soft IOL on a movable cylinder encompassing a fixed centrally located plunger having a knife edge;
   means for locating the IOL on the movable cylinder over the knife edge;
   means for inserting the operating ends of a pair of forceps into a hollow plastic tube and separating the forceps thereby stretching the tube;
   means for placing the stretched tube over the IOL and pushing the stretched tube in a downward direction against the IOL thereby causing the cylinder to move in a downward direction causing the IOL to fold about the knife edge located on the fixed plunger;
   means for closing the forceps about the knife edge thereby folding the plastic tube about the folded IOL;
   means for inserting the folded lens and the tube through a suitable incision in the eye;
   means for opening the forceps allowing the lens and the hollow tube to unfold; and
   means for removing the hollow tube and repositioning the lens.

27. A system according to claim 26 in which said plastic tube has a tab located on only one side and in which the forceps are inserted into the hollow tube from the side having the tab.

28. A system according to claim 27 in which said hollow tube is removed by means of said tab.

* * * * *